United States Patent
Cannell et al.

(10) Patent No.: US 7,622,104 B2
(45) Date of Patent: Nov. 24, 2009

(54) METHODS FOR RELAXING AND RE-WAVING HAIR COMPRISING AT LEAST ONE REDUCING AGENT AND AT LEAST ONE HYDROXIDE COMPOUND

(75) Inventors: David W. Cannell, Plainfield, NJ (US); Nghi Van Nguyen, Edison, NJ (US)

(73) Assignee: L'Oreal S.A., Paris (FR)

( * ) Notice: Subject to any disclaimer, the term of this patent is extended or adjusted under 35 U.S.C. 154(b) by 1890 days.

(21) Appl. No.: 09/931,919

(22) Filed: Aug. 20, 2001

(65) Prior Publication Data
US 2003/0079300 A1    May 1, 2003

(51) Int. Cl.
*A61K 7/135*    (2006.01)
*A61Q 5/04*    (2006.01)

(52) U.S. Cl. .................. 424/70.2; 424/70.4; 424/70.23; 424/70.14; 424/70.51; 424/70.24; 424/60; 424/62; 424/63

(58) Field of Classification Search ............ 8/405; 424/71, 72, 70.1, 70.2, 62, 60, 63, 70.6, 613, 424/616, 70.23, 70.24, 70.4, 70.51, 70.14
See application file for complete search history.

(56) References Cited

U.S. PATENT DOCUMENTS

| | | | | |
|---|---|---|---|---|
| 2,719,104 A | * | 9/1955 | Westerberg ............... | 8/432 |
| 4,174,952 A | * | 11/1979 | Cannell et al. ............. | 436/534 |
| 4,192,863 A | | 3/1980 | Kondo | |
| 4,301,820 A | * | 11/1981 | Cannell et al. ............. | 132/204 |
| 4,424,820 A | * | 1/1984 | Cannell et al. ............. | 132/204 |
| 4,635,654 A | * | 1/1987 | Mathews et al. ........... | 132/200 |
| 4,659,566 A | * | 4/1987 | Petrow ...................... | 424/70.5 |
| 4,793,992 A | * | 12/1988 | Mathews et al. ........... | 424/538 |
| 4,793,994 A | * | 12/1988 | Helioff et al. .............. | 424/70.4 |
| 4,814,351 A | * | 3/1989 | Mathews et al. ........... | 514/566 |
| 4,816,246 A | * | 3/1989 | Mathews et al. ........... | 424/70.5 |
| 4,840,791 A | * | 6/1989 | Mathews et al. ........... | 424/70.5 |
| 4,898,726 A | | 2/1990 | Beste | |
| 4,963,349 A | * | 10/1990 | Mathews et al. ........... | 424/70.5 |
| 4,992,267 A | | 2/1991 | DenBeste et al. | |
| 5,047,233 A | * | 9/1991 | Mathews et al. ........... | 424/70.2 |
| 5,356,439 A | * | 10/1994 | Schultz et al. .............. | 8/432 |
| 5,461,925 A | * | 10/1995 | Nguyen et al. ............. | 73/789 |
| 5,681,554 A | * | 10/1997 | Cannell et al. ............. | 424/70.14 |
| 5,783,175 A | * | 7/1998 | Schultz et al. .............. | 424/62 |
| 5,956,139 A | * | 9/1999 | Meyer et al. ............... | 356/338 |
| 6,013,250 A | * | 1/2000 | Cannell et al. ............. | 424/70.51 |
| 6,015,574 A | * | 1/2000 | Cannell et al. ............. | 424/450 |
| 6,058,943 A | | 5/2000 | Davis-Harris | |
| 6,221,389 B1 | * | 4/2001 | Cannell et al. ............. | 424/450 |
| 6,426,065 B1 | * | 7/2002 | Coope ....................... | 424/70.5 |
| 6,428,580 B2 | * | 8/2002 | Schultz et al. .............. | 8/406 |
| 6,435,193 B1 | * | 8/2002 | Cannell et al. ............. | 132/203 |
| 6,436,436 B1 | * | 8/2002 | Nguyen et al. ............. | 424/450 |
| 6,440,456 B1 | * | 8/2002 | Nguyen et al. ............. | 424/450 |
| 6,469,787 B1 | * | 10/2002 | Meyer et al. ............... | 356/342 |
| 6,486,105 B1 | * | 11/2002 | Cannell et al. ............. | 510/124 |
| 6,524,614 B2 | * | 2/2003 | Cannell et al. ............. | 424/450 |
| 6,558,697 B2 | * | 5/2003 | Cannell et al. ............. | 424/450 |
| 6,562,327 B1 | * | 5/2003 | Nguyen et al. ............. | 424/70.2 |
| 6,572,843 B1 | * | 6/2003 | Sorensen et al. ........... | 424/62 |
| 6,782,895 B2 | * | 8/2004 | Van Nguyen et al. ...... | 132/203 |
| 6,792,954 B2 | * | 9/2004 | Cannell et al. ............. | 132/203 |
| 6,800,277 B2 | * | 10/2004 | Van Nguyen et al. ...... | 424/70.2 |
| 6,800,302 B2 | * | 10/2004 | Cannell et al. ............. | 424/702 |
| 6,861,077 B1 | * | 3/2005 | Cannell et al. ............. | 424/725 |

FOREIGN PATENT DOCUMENTS

EP    0 712 623    5/1996

OTHER PUBLICATIONS

S. Ogawa et al. A curing method for permanent hair straightening using thioglycolic and dithiodiglycolic acids, *Journal of Cosmetic Science*, 51, 379-399 (Nov./Dec. 2000).
Co-pending U.S. Appl. No. 09/789,667—Title: Hair Relaxer Compositions Comprising at Least One Hydroxide Compound and at Least One Activating Agent, and Methods of Using the Same Inventors: David W. Cannell et al., filed Feb. 22, 2001.
Co-pending U.S. Appl. No. 09/516,942—Title: Hair Relaxer Compositions Utilizing Complexing Agent Activators Inventors: Nghi Van Nguyen et al., filed Mar. 1, 2000.
Co-pending U.S. Appl. No. 09/931,913—Title: Compositions Comprising at Least One Hydroxide Compound and at Least One Oxidizing Agent, and Methods to Straighten Curly Hair Inventors: Nghi Van Nguyen et al., filed Apr. 20, 2001.

(Continued)

*Primary Examiner*—Sabiha Qazi
(74) *Attorney, Agent, or Firm*—Finnegan, Henderson, Farabow, Garrett & Dunner LLP

(57) ABSTRACT

Methods and kits for lanthionizing keratin fibers to achieve relaxation of the keratin fibers, and methods and kits for re-waving keratin fibers comprising applying to keratin fibers a pretreatment composition comprising at least one reducing agent chosen from thiols, sulfites, and derivatives thereof, applying to the pretreated keratin fibers a composition comprising at least one hydroxide compound, and heating the keratin fibers.

35 Claims, No Drawings

OTHER PUBLICATIONS

Co-pending U.S. Appl. No. 09/838,197—Title: Composition and Methods for Lanthionizing Keratin Fibers Using at Least One Organic Nucleophile and at Least One Hydroxide Ion Generator Inventors: David W. Cannell et al., filed Apr. 20, 2001.

Co-pending U.S. Appl. No. 09/717,206—Title: Hair Relaxer Compositions Utilizing Cation Exchange Compositions Inventors: David W. Cannell et al., filed Nov. 22, 2001.

Co-pending U.S. Appl. No. 09/931,914—Title: Compositions Comprising at Least One Hydroxide Compound and at Least One Complexing Agent, and Methods for Using the Same Inventors: Nghi Van Nguyen et al., filed Aug. 20, 2001.

Co-pending U.S. Appl. No. 09/931,912—Title: Compositions Comprising at Least One Hydroxide Compound and at Least One Reducing Agent, and Methods for Relaxing Inventors: Nghi Van Nguyen et al., filed Aug. 20, 2001.

* cited by examiner

METHODS FOR RELAXING AND RE-WAVING HAIR COMPRISING AT LEAST ONE REDUCING AGENT AND AT LEAST ONE HYDROXIDE COMPOUND

The present invention is directed to lanthionizing keratin fibers to achieve relaxation of the keratin fibers, and also to re-waving keratin fibers using a combination of at least one hydroxide compound, at least one reducing agent chosen from thiols, sulfites, and derivatives thereof, and heat.

Straightening or relaxing the curls of very curly hair may increase the manageability and ease of styling of such hair. In today's market, there is an increasing demand for the hair care products referred to as "hair relaxers," which can relax or straighten naturally curly or kinky hair. Hair relaxers may either be applied in a hair salon by a professional or in the home by the individual consumer.

Hair fiber, a keratinous material, comprises proteins (polypeptides). Many of the polypeptides in hair fibers are bonded together or cross-linked with disulfide bonds (—S—S—). A disulfide bond may be formed from the reaction of two sulfhydryl groups (—SH), one on each of two cysteine residues, which results in the formation of a cystine residue. A cystine residue comprises a cross-link of the formula —$CH_2$—S—S—$CH_2$— between 2 polypeptides. While there are other types of bonds which occur between the polypeptides in hair fibers, such as ionic (salt) bonds, the permanent curling or the shape of the hair is essentially dependent on the disulfide bonds of cystine residues.

Generally, hair relaxing processes are chemical processes which may alter the aforementioned disulfide bonds between polypeptides in hair fibers and may form lanthionine residues [S[$CH_2$CH(NH—)(CO—)]$_2$]. Thus, the term "lanthionizing" is used when one skilled in the art refers to the relaxing of keratin fibers by hydroxide ions. "Lanthionizing," as used herein, refers to the formation of at least one lanthionine residue, which may accomplish, for example, any level of relaxation. "Relaxation" and "relaxing," as used herein, includes any level of relaxing, for example, from slight relaxing to straightening.

For example, hair fibers may be relaxed or straightened by disrupting the disulfide bonds of the hair fibers with an alkaline or reducing agent. The chemical disruption of disulfide bonds with such an agent is generally combined with mechanical straightening of the hair, such as combing, and straightening generally occurs due to changes in the relative positions of neighboring polypeptide chains within the hair fiber. This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. Generally, hydroxide ions initiate a reaction in which a cystine cross-link (—$CH_2$—S—S—$CH_2$—) is broken and a lanthionine cross-link (—$CH_2$—S—$CH_2$—) is formed. The lanthionine cross-link is shorter than a cystine cross-link by one sulfur atom, and thus the net effect of the reaction is to reduce the distance between polypeptides. Amino acid analysis indicates that from 25 mole % to 40 mole % of cystine residues are converted to lanthionine residues.

One reaction sequence comprises at least one bimolecular nucleophilic substitution reaction wherein an available hydroxide ion directly attacks the disulfide linkage of a cystine residue. The result is the formation of lanthionine residues and HOS$^-$. See Zviak, C., *The Science of Hair Care*, pp. 185-186 (1986). The second reaction sequence comprises at least one β-elimination reaction initiated by the nucleophilic attack of an available hydroxide ion on a hydrogen atom bonded to a carbon atom that is in the β-position with respect to the disulfide bond of a cystine residue. Id. The result is the formation of a dehydroalanine residue which comprises a reactive double bond (=$CH_2$). The double bond of the dehydroalanine residue can then react with the thiol group of a cysteine residue to form a lanthionine residue. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid or minimize damage to the hair protein or skin. If such a step is required, an acidic shampoo may be used to neutralize residual alkali and remove it from the hair and scalp.

Hydroxide-containing alkaline agents also have other advantages. For example, alkaline agents, such as sodium hydroxide and guanidine hydroxide, do not have a highly objectionable odor or cause such an odor on treating the hair. Further, hydroxide-based straighteners generally have relatively fast processing times and good straightening of naturally curly or kinky hair. Additionally, the achieved straightening effect is more durable; i.e., less likely to revert to a curly state after shampooing and exposure to the elements than is hair straightened with some other straighteners.

Despite these advantages, certain hydroxide-containing alkaline agents may have disadvantages. These disadvantages may be heightened when the hydroxide-containing alkaline agent is sodium hydroxide. Specifically, the causticity of sodium hydroxide can adversely affect the condition of the hair, for example, leaving it in a brittle state and harsh to the touch. Additionally, prolonged or unnecessary exposure of hair to such a strong alkali can weaken, break and dissolve the hair. The mechanical properties of hair that has been lanthionized using hydroxide ion generating compositions demonstrate that, while the hair may not be significantly weaker due to the reduction in space between polypeptides (and in fact may have a high yield force), the hair may have a lower elongation before breaking. This "brittleness" of high yield force coupled with low elongation and inherently weaker points (where the hair had natural twists) can lead to breakage during grooming. Further, in some instances, such a strong alkali can discolor the natural color of the hair. For example, the tone of natural brown hair may be reddened and natural white or grey hair may be yellowed. Further, the natural sheen of the hair may be delustered.

Most frequently, commercial relaxing compositions are in the form of gels or emulsions that contain varying proportions of strong water-soluble bases, such as sodium hydroxide (NaOH), or of compositions that contain slightly-soluble metal hydroxides, such as calcium hydroxide (Ca(OH)$_2$), which can be converted in situ to soluble bases, such as guanidine hydroxide. Traditionally, the two main hair relaxers used in the hair care industry for generating hydroxide ions are referred to as "lye" (lye=sodium hydroxide) relaxers and "no lye" relaxers.

The "lye" relaxers generally comprise sodium hydroxide in a concentration ranging from 1.5% to 2.5% by weight relative to the total weight of the composition (0.38M-0.63 M) depending on the carrier used, the condition of the hair fibers and the desired length of time for the relaxation process.

While "no lye" relaxers may not contain lye, they may, however, rely on the soluble hydroxides of inorganic metals, such as potassium hydroxide and lithium hydroxide. Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

Reducing agents, such as compounds comprising at least one thiol group, may also relax or straighten hair by disrupting disulfide bonds of the hair fibers. More commonly, reducing agents, such as thioglycolates, sulfites, cysteines and their derivatives, are used for texturizing purposes in hair straightening or relaxing compositions.

Processes comprising the application of these reducing agents generally require two steps: (1) a reducing step comprising the use of the reducing agent, and (2) a neutralizing step comprising the use of an oxidizing composition. The reaction with the reducing agent is normally initiated by thiolate ions. Generally, the higher the concentration of the thiolate ions in the composition, the faster the straightening or relaxing reaction will occur. See Zviak at page 190. This concentration, and therefore the rate of the reaction, are dependent on the ionization constant $K_i$ of the thiol used. Thus, the pK value of a particular thiol expresses the nature of the thiol and determines both the equilibrium level and, therefore, the concentration of thiolate ions at a given pH. For example, reducing agents are generally used in a concentration of about 5% at a pH ranging from 9 to 10.

The reducing step is generally a reversible reduction reaction of disulfide bonds within a keratin fiber which can be represented by the following reaction scheme, wherein k represents the keratin protein chain of a keratin fiber, and RSH represents a thiol containing reducing agent:

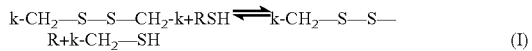

(I)

(II)

Generally, the disulfide product, RS—SR, and any residual reducing agent, RSH, are rinsed from the hair, and then the disulfide bonds are restored in the neutralizing step. The neutralizing step can be represented by the following reaction scheme:

(III)

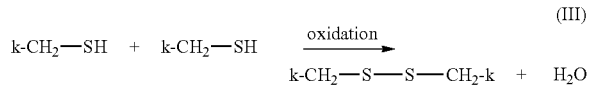

These reducing agents may have disadvantages not present with alkaline agents. As described above, thiol-based relaxing may require the use of an oxidizing neutralizer, such as hydrogen peroxide, to chemically relink the hair keratin disulfide bonds and stop the relaxation process quickly. As the thiol-reduced hair is in an alkaline state, any excess neutralizer must also be removed to avoid bleaching the natural color of the hair. As with hydroxide-containing alkaline agents, a high concentration of reducing agent may result in hair damage, and a low concentration may result in reversion of the hair to its original curly state (i.e., non-durable relaxation).

Some strides have been made to improve to the condition of sodium hydroxide-straightened hair by incorporating an auxiliary hair keratin disulfide reducing agent having a sulfhydryl functional group available chosen from cysteine, homologs of cysteine, and water soluble derivatives of cysteine. See, e.g, U.S. Pat. No. 4,992,267, the disclosure of which is incorporated herein by reference. This patent discloses the use of sodium hydroxide at concentrations of between about 1 weight percent to about 2.5 weight percent, such as between about 1.5 weight percent and about 2.25 weight percent relative to the total concentration of the composition.

Further, co-pending U.S. patent application Ser. No. 09/789,667, the disclosure of which is incorporated herein by reference, discloses compositions, and methods for using these compositions, for lanthionizing keratin fibers comprising at least one hydroxide compound with the proviso that the at least one hydroxide compound is not sodium hydroxide, lithium hydroxide or potassium hydroxide and at least one activating agent chosen from cysteine-based compounds. These compositions may make it possible to decrease the amount of the at least one hydroxide compound needed even further while maintaining good hair condition.

The use of certain reducing agents and certain hydroxide-based compounds has previously been disclosed. A curing method for permanent hair straightening using thioglycolic acid, dithioglycolic acid, and potassium hydroxide is known. See Ogawa, S. et al., *J. Cosmet. Sci.*, 51, 379-399 (2000). This method comprises three steps: (1) reduction using thioglycolic acid (3% to 9%), dithioglycolic acid, potassium hydroxide (1.05%), EDTA and monoethanolamine; (2) heat treatment, followed by (3) oxidation of the hair. Further, for example, a process for imparting smoothness, body and a permanent wave pattern is also known. See U.S. Pat. No. 6,058,943. This process comprises at least eleven steps such aqueous alkaline relaxant composition containing an alkaline hydroxide reducing agent to the hair (step "(a)"), applying an aqueous waving composition containing a thioglycolate reducing agent to the hair (step "(d)"), and shampooing and rinsing the hair with a neutralizing shampoo and water (step "(h)").

The present invention relates to a method for relaxing keratin fibers without damaging the fibers but at the same time without substantial reversion to the original curly state of the hair using compositions comprising low concentrations of at least one hydroxide compound and compositions comprising at least one reducing agent. Further, lanthionizing processes which allow re-waving of relaxed hair are disclosed. Hair which has been relaxed using currently available reducing agents cannot thereafter be permed because the disulfide bonds in the hair have been irreversibly altered by the lanthionizing treatment.

Thus, the present invention provides, in one embodiment, a method for lanthionizing keratin fibers to achieve relaxation of the keratin fibers comprising (i) applying a pretreatment composition, wherein the pretreatment composition comprises at least one reducing agent chosen from thiols, sulfites, and derivatives thereof to keratin fibers for a sufficient period of time to reduce at least one keratin bond in the keratin fibers; (ii) rinsing the keratin fibers; (iii) generating hydroxide ions in at least one solvent, wherein the step of generating comprises including at least one hydroxide compound in the at least one solvent; (iv) applying a composition comprising the generated hydroxide ions to the pre-treated keratin fibers for a sufficient period of time to lanthionize at least one keratin fiber; (v) heating the keratin fibers; and (vi) terminating the lanthionization when the keratin fibers are relaxed.

The present invention also provides a method for re-waving keratin fibers comprising (i) applying a pretreatment composition, wherein the pretreatment composition comprises at least one reducing agent chosen from thiols, sulfites, and derivatives thereof to keratin fibers for a sufficient period of time to reduce at least one keratin bond in the keratin fibers; (ii) rinsing the keratin fibers; (iii) generating hydroxide ions in at least one solvent, wherein the step of generating comprises including at least one hydroxide compound in the at least one solvent; (iv) applying a composition comprising the generated hydroxide ions to the pre-treated keratin fibers for a sufficient period of time to lanthionize at least one of the keratin fibers; (v) heating the keratin fibers; (vi) terminating the lanthionization, and (vii) applying a permanent waving composition to the lanthionized keratin fibers for a sufficient period of time to permanently wave the keratin fibers.

Further, the present invention also provides for a multicomponent kit for lanthionizing keratin fibers, wherein the kit comprises at least two compartments. A first compartment of the kit contains at least one hydroxide compound, and a second compartment contains at least one reducing agent chosen from thiols, sulfites, and derivatives thereof.

The present invention also provides for a multicomponent kit for re-waving keratin fibers, wherein the kit comprises at least three components. A first compartment contains at least one hydroxide compound; a second compartment contains at least one reducing agent chosen from thiols, sulfites, and derivatives thereof; and a third compartment contains a permanent waving composition.

Certain terms used herein are defined below:

As used herein, "at least one" means one or more and thus includes individual components as well as mixtures/combinations.

"Keratin fibers" as defined herein may be human keratin fibers, and may be chosen from, for example, hair.

"Heating" refers to the use of elevated temperature (i.e., above 100° C.). In one embodiment, the heating in the inventive method may be provided by directly contacting the keratin fibers with a heat source, e.g., by heat styling of the keratin fibers. Non-limiting examples of heat styling by direct contact with the keratin fibers include flat ironing, and curling methods using elevated temperatures (such as, for example, curling with a curling iron and/or hot rollers). In another embodiment, the heating in the inventive method may be provided by heating the keratin fibers with a heat source which may not directly contact the keratin fibers. Non-limiting examples of heat sources which may not directly contact the keratin fibers include blow dryers, hood dryers, heating caps and steamers.

"Re-waving" as used herein refers to a process comprising relaxing keratin fibers and subsequently permanent waving the relaxed keratin fibers.

"Permanent waving" and "permanently waving," as used herein, include any level of waving, such as, for example, from a body wave to ringlets.

It is to be understood that both the foregoing general description and the following detailed description are exemplary and explanatory only and are not restrictive of the invention as claimed.

As described above, the lanthionization of keratin fibers is believed to be driven by the disruption of the disulfide bonds of cystine residues in the fibers. The compositions and methods of the present invention may, in one embodiment, provide a novel way of generating sufficient available hydroxide ions from at least one hydroxide compound to effectively relax the hair using low concentrations of the at least one hydroxide compound and of at least one reducing agent. For example, the concentration of the at least one hydroxide compound required for effective relaxation using the inventive compositions may be lower than the concentration required to effectively relax the hair using at least one hydroxide compound without at least one reducing agent. Further, such compositions may be capable of relaxing the keratin fibers without damaging the fibers. This is particularly true when the compounds are applied to the hair, and then the hair is heated.

Thus, the present invention provides, in one embodiment, a method for lanthionizing keratin fibers to achieve relaxation of the keratin fibers comprising (i) applying a pretreatment composition comprising at least one reducing agent chosen from thiols, sulfites, and derivatives thereof to keratin fibers for a sufficient period of time to reduce at least one keratin bond in the keratin fibers; (ii) rinsing the keratin fibers; (iii) generating hydroxide ions in at least one solvent, wherein the step of generating comprises including at least one hydroxide compound in the at least one solvent; (iv) applying a composition comprising the generated hydroxide ions to the pre-treated keratin fibers for a sufficient period of time to lanthionize at least one keratin fiber; (v) heating the keratin fibers; and (vi) terminating the lanthionization when the keratin fibers are relaxed. In one embodiment, the method further comprises shampooing the keratin fibers subsequent to heating the keratin fibers. The method may further comprise rinsing the keratin fibers prior to and/or subsequent to shampooing the keratin fibers.

The present invention also provides a method for re-waving keratin fibers comprising steps (i) to (vi) above, and then (vii) applying a permanent waving composition to the lanthionized keratin fibers for a sufficient period of time to permanently wave at least one keratin fiber. In one embodiment, the method further comprises rolling the lanthionized keratin fibers onto at least one curling rod after prior to or following the application of the permanent waving composition. In another embodiment, the method further comprises rinsing the rolled keratin fibers after a sufficient period of time to permanently wave at least one of the rolled keratin fibers.

Further, the present invention also provides for multicompartment kits for lanthionizing or re-waving keratin fibers. The lanthionizing kit comprises at least two compartments. A first compartment of the kit contains at least one hydroxide compound, and a second compartment contains at least one reducing agent chosen from thiols, sulfites, and derivatives thereof. The re-waving kit comprises at least three compartments. A first compartment contains at least one hydroxide compound; a second compartment contains at least one reducing agent chosen from thiols, sulfites, and derivatives thereof; and a third compartment contains a permanent waving composition.

Not to be limited to theory, the inventors believe that, by using a pretreatment composition comprising at least one reducing agent, the reducing reaction may be confined to the formation of a cysteine residue, k-$CH_2$—SH, and the mixed disulfide, k-$CH_2$—S—S—R, (i.e., Equation (I)). Thus, when the keratin fibers are rinsed following a sufficient time to allow the at least one reducing agent to penetrate the keratin fiber, the reducing reaction (i.e., Equation (I)) may be largely reversed, leaving low concentrations of the mixed disulfide and the cysteine residue. Thus, the relaxing capability of the composition comprising at least one hydroxide compound (which is subsequently applied) may be increased by breaking at least some of the cystine disulfide bonds in the keratin fibers and forming the cysteine residue using the pretreatment composition, and by the use of heat. Thus, the heat and the presence of the cysteine residues may catalyze the rearrangement of the protein rearrangement and lanthionization within a keratin fiber. Therefore, low concentrations of the at least one hydroxide compound may be sufficient to effect relaxation of the keratin fibers. Further, the use of the pretreatment composition comprising at least one reducing agent may result in fewer lanthionine cross-links because of the products formed in the reducing reaction of Equation I, and therefore, at least one of the mechanical properties, such as tensile strength, of the treated hair may be better than that of hair treated using conventional methods.

According to the present invention, the at least one hydroxide compound may be chosen from any compound comprising at least one hydroxide group which may at least partially dissociate into a counterion and a hydroxide ion in solution. Non-limiting examples of the at least one hydroxide compound include alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable. Other non-limiting examples of the at least one hydroxide compound include sodium hydroxide, potassium hydroxide, lithium hydroxide, rubidium hydroxide, cesium hydroxide, francium hydroxide, beryllium hydroxide, magnesium hydroxide, calcium hydroxide, strontium hydroxide, barium hydroxide, cupric hydroxide, molybdenum hydroxide, manganese hydroxide, zinc hydroxide, cobalt hydroxide, nickel hydroxide, cadmium hydroxide, gold hydroxide, lanthanum hydroxide, cerium hydroxide, actinium hydroxide, thorium hydroxide, aluminum hydroxide, guanidine hydroxides and quaternary ammonium hydroxides. The at least one hydroxide compound can also be chosen from those formed in situ, such as, for example, guanidine hydroxide. As previously mentioned, guanidine hydroxide may be formed in situ, for example, from the reaction of calcium hydroxide and guanidine carbonate.

According to the present invention, the at least one hydroxide compound is generally present in an amount sufficient to effect relaxation and/or straightening, i.e., lanthionization, of the keratin fibers without damaging the fibers. According to the present invention, the at least one hydroxide compound is present in an amount such that the amount of hydroxide ion generally ranges from 0.01% to 2.5% by weight relative to the total weight of the composition, such as from 0.1% to 1% by weight.

The at least one reducing agent of the present invention is chosen from thiols, sulfites, and derivatives thereof. As used herein, derivatives include salts. The at least one reducing agent may be chosen from thiols, sulfites and derivatives thereof such as, for example, those listed in the *International Cosmetic Ingredient Dictionary and Handbook*, 8$^{th}$ Ed., Vol. 2 (2000) at page 1767. Non-limiting examples of suitable thiols are thioglycolates, thiolactates, thiolglycerols, thiocarboxylic acids, thioesters, thioamides, alkyl mercaptans, and cysteines. In one embodiment, the at least one reducing agent is chosen from thioglycolates, and in yet another embodiment, the at least one reducing agent is monoethanolamine thioglycolate. Non-limiting examples of suitable sulfites are hydrogen sulfite, organic sulfites such as alkyl sulfites (such as dimethyl sulfite and diethyl sulfite) and alkylene sulfites (such as glycol sulfite, 1,2-propyleneglycol sulfite, and 1,3-butyleneglycol sulfite), and inorganic sulfites (such as ammonium sulfite, magnesium hydrogen sulfite, potassium sulfite, sodium sulfite, sodium hydrogen sulfite, silver sulfite, and zinc sulfite).

According to the present invention, the at least one reducing agent is generally present in an amount sufficient to complement the relaxing and/or straightening effects of the at least one hydroxide compound such that the keratin fibers are relaxed. According to the present invention, the at least one reducing agent is present in an amount generally ranging from 0.1% to 5% by weight relative to the total weight of the composition, such as from 0.5% to 2.5% by weight. The aforementioned amounts were calculated based on monoethanolamine thioglycolate as the at least one reducing agent. One of skill in the art may adjust the amounts according to the particular at least one reducing agent chosen.

Permanent waving compositions useful in the present invention may be chosen from any known permanent waving composition. Further, according to the present invention, the at least one solvent can be chosen from solvents commonly used in compositions for the hair. Non-limiting examples of the at least one solvent include water and solvents which may lower the ionic bonding forces in the solute molecules enough to cause at least partial separation of their constituent ions, such as dimethyl sulfoxide (DMSO). In one embodiment, the at least one solvent is chosen from water and DMSO. The at least one solvent can be present in an amount sufficient to ensure that, upon mixing, enough of the generated available hydroxide ions remain soluble in order to effect lanthionization of keratin fibers.

The compositions of the present invention as well as those used in the methods of the present invention may further comprise at least one suitable additive chosen from additives commonly used in hair relaxing compositions. Non-limiting examples of the at least one suitable additive include dyes, anionic surfactants, cationic surfactants, nonionic surfactants, amphoteric surfactants, fragrances, screening agents, chelating agents, preserving agents, proteins, vitamins, silicones, polymers such as thickening polymers, plant oils, mineral oils, synthetic oils and any other additive conventionally used in compositions for the care and/or treatment of hair.

The compositions of the present invention may be provided in the form of a multicompartment kit. According to one embodiment of the present invention, the multicompartment kit for lanthionizing keratin fibers may comprise at least two separate compartments. A first compartment of the kit may comprise a first composition containing at least one hydroxide compound. This first composition can be in a form chosen from an emulsion, suspension, solution, gel, cream, and a paste. A second compartment of the kit can comprise a pretreatment composition comprising at least one reducing agent. This composition may be in a form chosen from an emulsion, suspension, solution, gel, cream, and paste. The skilled artisan, based on the stability of the composition and the application envisaged, will be able to determine how the multicompartment compositions should be stored and mixed.

The present invention also provides for a multicompartment kit for re-waving keratin fibers, wherein the kit comprises at least three compartments. A first compartment contains at least one hydroxide compound; a second compartment contains at least one reducing agent chosen from thiols, sulfites, and derivatives thereof; and a third compartment contains a permanent waving composition.

Other than in the operating example, or where otherwise indicated, all numbers expressing quanities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLES

Unless otherwise noted, the procedure used to treat the hair and measure the relaxing efficiency (%RE) is as follows: Natural kinky hair was treated with a solution containing from 1% to 3% monoethanolamine thioglycolate (MEA-TGA) (a reducing agent) having a pH ranging from 5 to 9 for a period of time ranging from 2 minutes to 10 minutes, and then the hair was rinsed with water for 1 minute. The reduced hair was then placed in a solution containing from 0.3% to 1.0% sodium hydroxide (NaOH) (a hydroxide compound) for 3 minutes, and then the hair was blotted dry. A flat iron was used to straighten the hair for 10 seconds. The straightened hair was shampooed and then placed in a humidity chamber at 90% Relative Humidity (%RH) for at least 24 hours. The percent Relaxing Efficiency (%RE) is defined as:

$$\%RE = (L_f/L_t) \times 100$$

where $L_f$=length of the relaxed hair after 24 hours at 90% RH $L_t$=length of the hair at the straight configuration The greater the relaxing efficiency (% RE), the straighter the hair after treatment.

Example 1

The Effect of the pH of the Thioglycolate Solution on the Relaxing Efficiency

Following the above procedure, natural ethnic hair was treated first with a solution containing 5% MEA-TGA having a pH as shown in Table 1, then with a solution comprising an amount of sodium hydroxide as shown in Table 1, and then the relaxing efficiency was determined. The results are shown in Table 1.

TABLE 1

Relaxing Efficiency (% RE) of Hair Treated with Thioglycolate Solutions at Different pHs and with Various Sodium Hydroxide Solutions

| pH of Composition Comprising 5% MEA-TGA | Amount of NaOH (%) | | | |
|---|---|---|---|---|
| | 0.3 | 0.5 | 0.7 | 1.0 |
| 5.2 | 62% | 64% | 71% | 87% |
| 7.0 | 63% | 68% | 86% | 89% |
| 9.0 | 89% | 91% | 95% | 96% |

A high relaxation efficiency after 24 hours under 90% relative humidity indicates that the hair did not display reversion. Thus, the data show that hair can be effectively relaxed without substantial reversion after being treated with a solution containing a low concentration of monoethanolamine thioglycolate and a solution containing a low concentration of NaOH and then subjected to heat. Monoethanolamine thioglycolate solutions having a higher pH resulted in a higher relaxation efficiency.

Example 2

The Effect of the Concentration of Thioglycolate Solution on the Relaxing Efficiency Following the above procedure, natural ethnic hair was treated first with a solution containing an amount of MEA-TGA as shown in Table 2 having pH 9.0 for 10 minutes, then with a solution containing an amount of sodium hydroxide as shown in Table 2, and then the relaxing efficiency was determined. The results are shown in Table 2.

TABLE 2

Relaxing Efficiency (% RE) of Hair Treated with Thioglycolate Solutions at Different Concentrations and with Various Sodium Hydroxide Solutions

| Amount of MEA-TGA (%) | Amount of NaOH (%) | | | |
|---|---|---|---|---|
| | 0.3 | 0.5 | 0.7 | 1.0 |
| 1 | 50% | 63% | 68% | 79% |
| 3 | 80% | 83% | 87% | 96% |
| 5 | 89% | 91% | 95% | 96% |

The high relaxation efficiency after 24 hours under 90% relative humidity indicates that the hair did not display reversion. The data show that hair can be effectively relaxed without substantial reversion after being treated with a solution containing a low concentration of monoethanolamine thioglycolate and a solution containing a low concentration of NaOH, and then subjected to heat.

Example 3

The Effect of the Length of Time for Treatment with a Thioglycolate Solution on the Relaxing Efficiency Following the above procedure, natural ethnic hair was treated first with a solution containing 3% MEA-TGA having pH 9.0 for the length of time shown in Table 3, then with a solution containing 0.3% sodium hydroxide, and then the relaxing efficiency was determined. The results are shown in Table 3.

TABLE 3

Relaxing Efficiency (% RE) of Hair Treated with Thioglycolate Solutions for Various Lengths of Time

| Length of Treatment Time (seconds) | Relaxing Efficiency (% RE) |
|---|---|
| 60 | 50% |
| 90 | 60% |
| 120 | 82% |

The high relaxation efficiency after 24 hours under 90% relative humidity indicates that the hair did not display reversion. The data show that hair can be effectively relaxed without substantial reversion after being treated with a solution containing a low concentration of monoethanolamine thioglycolate for 2 minutes, a solution containing a low concentration of NaOH, and then subjected to heat.

Example 4

Permability of Relaxed Hair

Natural kinky hair was treated with a solution containing 3% MEA-TGA at a pH of 9 for 10 minutes, and then the hair was rinsed with water for 1 minute. The reduced hair was then placed in a solution containing an amount of sodium hydroxide shown in Table 4 for 1 minute, and then the hair was blotted dry. The straightened hair was shampooed and placed in a humidity chamber at 90% relative humidity for at least 24 hours. The relaxing efficiency (%RE) was about 80-96%. The straight hair was wrapped around a perm rod and treated with a commercial perm solution following the accompanying instructions. For the control, natural kinky hair was first relaxed with a commercially available lye relaxer, and then permed. Each sample of the permed hair was then removed from the rod and placed in a humidity chamber at 90% relative humidity for at least 24 hours. The percent Perming Efficiency (%PE) is defined as:

%PE=$(L_r/L_p)$×100 where $L_p$=length of the permed hair after 24 hours at 90% RH
$L_r$=length of the hair before the perm
The greater the perming efficiency (% PE), the curlier the hair after perming. The results are shown in Table 4.

TABLE 4

Perming Efficiency (% PE) of Hair Treated with a Thioglycolate Solution, a Sodium Hydroxide Solution, Heat and then Permed

|      | Control | Amount of NaOH in Sodium Hydroxide Solution (%) | | | |
|------|---------|-----|-----|-----|-----|
|      |         | 0.3 | 0.5 | 0.7 | 1.0 |
| % PE | 22%     | 62% | 64% | 52% | 50% |

The high perming efficiency after 24 hours under 90% relative humidity indicates that the hair relaxed using the inventive method prior to perming is permable. Hair relaxed using a commercially available lye relaxer prior to perming displayed poor perming efficiency.

What is claimed is:

1. A method for lanthionizing keratin fibers to achieve relaxation of said keratin fibers comprising:
   (i) applying a pretreatment composition to said keratin fibers, wherein said pretreatment composition comprises at least one reducing agent chosen from thioglycolates for a sufficient period of time to reduce at least one keratin bond in said keratin fibers;
   (ii) rinsing said keratin fibers;
   (iii) generating hydroxide ions in at least one solvent, wherein said step of generating comprises including at least one hydroxide compound in said at least one solvent;
   (iv) applying a composition comprising said generated hydroxide ions to said keratin fibers for a sufficient period of time to lanthionize at least one of said keratin fibers;
   (v) heating said keratin fibers; and
   (vi) terminating said lanthionization when said keratin fibers are relaxed.

2. A method according to claim 1, further comprising shampooing said keratin fibers subsequent to said heating.
3. A method according to claim 2, further comprising rinsing said keratin fibers subsequent to said shampooing.
4. A method according to claim 2, further comprising rinsing said keratin fibers prior to said shampooing.
5. A method according to claim 1, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable.
6. A method according to claim 5, wherein said at least one hydroxide compound is chosen from sodium hydroxide, lithium hydroxide, and potassium hydroxide.
7. A method according to claim 6, wherein said at least one hydroxide compound is sodium hydroxide.
8. A method according to claim 1, wherein the at least one hydroxide compound is present in an amount ranging from 0.01% to 2.5% by weight, relative to the total weight of said composition.
9. A method according to claim 8, wherein the at least one hydroxide compound is present in an amount ranging from 0.1% to 1% by weight relative to the total weight of said composition.
10. A method according to claim 1, wherein said thioglycolates are monoethanolamine thioglycolate.
11. A method according to claim 1, wherein said at least one reducing agent is present in an amount ranging from 0.1% to 5% by weight relative to the total weight of the composition.
12. A method according to claim 11, wherein said at least one reducing agent is present in an amount ranging from 0.5% to 2.5% by weight relative to the total weight of the composition.
13. A method according to claim 1, wherein said at least one solvent is chosen from DMSO and water.
14. A method according to claim 1, wherein said composition further comprises at least one additive chosen from dyes, anionic surfactants, cationic surfactants, nonionic surfactants, amphoteric surfactants, fragrances, silicones, silicone derivatives, screening agents, chelating agents, preserving agents, proteins, vitamins, plant oils, mineral oils and synthetic oils.
15. A method according to claim 1, wherein said composition is in a form chosen from an oil-in-water emulsion, a water-in-oil emulsion, a dispersion, a suspension, a cream, a foam, a gel, a spray, a powder and a liquid.
16. A method according to claim 1, wherein said keratin fibers are hair.
17. A method for re-waving keratin fibers comprising:
   (i) applying a pretreatment composition to said keratin fibers comprising at least one reducing agent chosen from thioglycolates to keratin fibers for a sufficient period of time to reduce at least one keratin bond in said keratin fibers;
   (ii) rinsing said keratin fibers;
   (iii) generating hydroxide ions in at least one solvent, wherein said step of generating comprises including at least one hydroxide compound in said at least one solvent;
   (iv) applying a composition comprising said generated hydroxide ions to said keratin fibers for a sufficient period of time to lanthionize at least one of said keratin fibers;

(v) heating said keratin fibers;
(vi) terminating said lanthionization, and
(vii) applying a permanent waving composition to said keratin fibers for a sufficient period of time to permanently wave at least one of said keratin fibers.

18. A method according to claim 17, further comprising shampooing said keratin fibers subsequent to said heating.

19. A method according to claim 18, further comprising rinsing said keratin fibers subsequent to said shampooing.

20. A method according to claim 18, further comprising rinsing said keratin fibers prior to said shampooing.

21. A method according to claim 17, further comprising rolling said lanthionized keratin fibers onto at least one curling rod prior to or subsequent to said application of said permanent waving composition.

22. A method according to claim 21, further comprising rinsing said rolled keratin fibers after a sufficient period of time to permanently wave said rolled keratin fibers.

23. A method according to claim 17, wherein said at least one hydroxide compound is chosen from alkali metal hydroxides, alkaline earth metal hydroxides, transition metal hydroxides, lanthanide metal hydroxides, actinide metal hydroxides, Group Ill hydroxides, Group IV hydroxides, Group V hydroxides, Group VI hydroxides, organic hydroxides, and compounds comprising at least one hydroxide substituent which is at least partially hydrolyzable.

24. A method according to claim 23, wherein said at least one hydroxide compound is chosen from sodium hydroxide, lithium hydroxide, and potassium hydroxide.

25. A method according to claim 24, wherein said at least one hydroxide compound is sodium hydroxide.

26. A method according to claim 17, wherein the at least one hydroxide compound is present in an amount ranging from 0.01 to 2.5% by weight, relative to the total weight of said composition.

27. A method according to claim 26, wherein the at least one hydroxide compound is present in an amount ranging from 0.1% to 1% by weight relative to the total weight of said composition.

28. A method according to claim 17, wherein said thioglycolates are monoethanolamine thioglycolate.

29. A method according to claim 17, wherein said at least one reducing agent is present in an amount ranging from 0.1% to 5% by weight relative to the total weight of the composition.

30. A method according to claim 20, wherein said at least one reducing agent is present in an amount ranging from 0.5% to 2.5% by weight relative to the total weight of the composition.

31. A method according to claim 17, wherein said at least one solvent is chosen from DMSO and water.

32. A method according to claim 17, wherein said composition further comprises at least one additive chosen from dyes, anionic surfactants, cationic surfactants, nonionic surfactants, amphoteric surfactants, fragrances, silicones, silicone derivatives, screening agents, preserving agents, proteins, vitamins, plant oils, mineral oils and synthetic oils.

33. A method according to claim 17, wherein said composition is in a form chosen from an oil-in-water emulsion, a water-in-oil emulsion, a dispersion, a suspension, a cream, a foam, a gel, a spray, a powder and a liquid.

34. A method according to claim 17, wherein said keratin fibers are hair.

35. A multicompartment kit for re-waving keratin fibers comprising:
(a) a first compartment comprising a first composition,
(b) a second compartment comprising a second composition, and
(c) a third compartment comprising a third composition,
wherein said first composition comprises at least one hydroxide compound;
wherein said second composition comprises at least one reducing agent chosen from thioglycolates, and
wherein said third composition is a permanent waving composition.

* * * * *